United States Patent
Prisco et al.

(10) Patent No.: US 8,025,716 B2
(45) Date of Patent: Sep. 27, 2011

(54) FLUID DELIVERY SYSTEMS AND METHODS HAVING FLOATING BAFFLE AIDED AIR REMOVAL

(75) Inventors: Michael R. Prisco, Geneva, IL (US); Atif M. Yardimci, Vernon Hills, IL (US); Serhan Acikgoz, Des Planies, IL (US); James C. Laird, Grayslake, IL (US); Shincy J. Maliekkal, Glenview, IL (US); Justin B. Rohde, Des Plaines, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/030,624

(22) Filed: Feb. 18, 2011

(65) Prior Publication Data
US 2011/0137236 A1    Jun. 9, 2011

Related U.S. Application Data

(62) Division of application No. 11/865,577, filed on Oct. 1, 2007, now Pat. No. 7,892,332.

(51) Int. Cl.
*B01D 19/00*     (2006.01)
(52) U.S. Cl. .............................. 95/260; 95/262; 96/204
(58) Field of Classification Search .................. 95/262, 95/260; 96/204
See application file for complete search history.

(56) References Cited

U.S. PATENT DOCUMENTS

| | | |
|---|---|---|
| 250,868 A | 12/1881 | Abbott |
| 927,476 A | 7/1909 | Barker |
| 1,505,050 A | 8/1924 | Lauritsen |
| 2,292,007 A | 8/1942 | Morgan |
| 3,044,236 A | 7/1962 | Bearden et al. |
| 3,074,645 A | 1/1963 | Main |
| 3,095,062 A | 6/1963 | Neely |
| 3,229,445 A | 1/1966 | Kraft |
| 3,287,885 A | 11/1966 | Sommer |
| 3,295,297 A | 1/1967 | Collins |
| 3,342,019 A | 9/1967 | Smythe |
| 3,412,760 A | 11/1968 | Franck |
| 3,527,572 A | 9/1970 | Urkiewicz |
| 3,581,464 A | 6/1971 | Bhuta et al. |
| 3,598,727 A * | 8/1971 | Willock ..................... 210/177 |
| 3,677,710 A | 7/1972 | Hirsch |
| 3,744,492 A | 7/1973 | Leibinsohn |
| 3,769,207 A | 10/1973 | Baer |
| 3,771,288 A | 11/1973 | Wisman et al. |
| 3,795,088 A | 3/1974 | Esmond |
| 3,827,561 A | 8/1974 | Serfass et al. |
| 3,834,386 A | 9/1974 | Sisley |
| 3,849,071 A | 11/1974 | Kayser |

(Continued)

FOREIGN PATENT DOCUMENTS
CH    296007    1/1954
(Continued)

*Primary Examiner* — Duane Smith
*Assistant Examiner* — Douglas Theisen
(74) *Attorney, Agent, or Firm* — K&L Gates LLP

(57) ABSTRACT

A medical fluid delivery system includes a fluid disposable configured to hold and transport a medical fluid and an air separation chamber in fluid communication with the fluid disposable. The air separation chamber includes at least one fluid baffle floating within the air separation chamber and configured to separate air from medical fluid traveling through the chamber.

23 Claims, 6 Drawing Sheets

U.S. PATENT DOCUMENTS

| | | | |
|---|---|---|---|
| 3,898,045 A * | 8/1975 | Bowley | 422/46 |
| 3,908,653 A | 9/1975 | Kettering | |
| 3,964,479 A | 6/1976 | Boag et al. | |
| 3,976,311 A | 8/1976 | Spendlove | |
| 3,985,134 A | 10/1976 | Lissot et al. | |
| 3,996,027 A | 12/1976 | Schnell et al. | |
| 4,031,891 A | 6/1977 | Jess | |
| 4,031,894 A | 6/1977 | Jess | |
| 4,038,190 A | 7/1977 | Baudet et al. | |
| 4,047,563 A | 9/1977 | Kurata | |
| 4,048,995 A | 9/1977 | Mittleman | |
| 4,054,522 A | 10/1977 | Pinkerton | |
| 4,060,485 A | 11/1977 | Eaton | |
| 4,061,031 A | 12/1977 | Grimsrud | |
| 4,102,655 A | 7/1978 | Jeffery et al. | |
| 4,137,160 A | 1/1979 | Ebing et al. | |
| 4,149,860 A | 4/1979 | Kulik | |
| 4,151,088 A | 4/1979 | Wolf, Jr. et al. | |
| 4,191,182 A | 3/1980 | Popovich et al. | |
| 4,200,095 A | 4/1980 | Reti | |
| 4,293,413 A | 10/1981 | Schnell | |
| 4,304,670 A | 12/1981 | Watanabe et al. | |
| 4,311,137 A | 1/1982 | Gerard | |
| 4,325,715 A | 4/1982 | Bowman et al. | |
| 4,344,777 A | 8/1982 | Siposs | |
| 4,345,919 A | 8/1982 | Wilkinson et al. | |
| 4,345,999 A | 8/1982 | Sigdell et al. | |
| 4,353,368 A | 10/1982 | Slovak et al. | |
| 4,363,641 A | 12/1982 | Finn, III | |
| 4,368,118 A | 1/1983 | Siposs | |
| 4,427,009 A | 1/1984 | Wells et al. | |
| 4,433,971 A | 2/1984 | Lindsay et al. | |
| 4,486,188 A | 12/1984 | Altshuler et al. | |
| 4,493,705 A | 1/1985 | Gordon et al. | |
| 4,512,163 A | 4/1985 | Wells et al. | |
| 4,531,937 A | 7/1985 | Yates | |
| 4,568,333 A | 2/1986 | Sawyer et al. | |
| 4,583,981 A | 4/1986 | Urquhart et al. | |
| 4,586,925 A | 5/1986 | Carlsson et al. | |
| 4,622,032 A | 11/1986 | Katsura et al. | |
| 4,643,713 A | 2/1987 | Viitala | |
| 4,643,715 A | 2/1987 | Isono et al. | |
| 4,666,598 A | 5/1987 | Heath et al. | |
| 4,681,606 A | 7/1987 | Swan, Jr. et al. | |
| 4,715,398 A | 12/1987 | Shouldice et al. | |
| 4,722,725 A | 2/1988 | Sawyer et al. | |
| 4,722,731 A | 2/1988 | Vailancourt | |
| 4,734,269 A | 3/1988 | Clarke et al. | |
| 4,806,135 A | 2/1989 | Siposs | |
| 4,932,987 A | 6/1990 | Molina | |
| 4,941,875 A | 7/1990 | Brennan | |
| 4,946,439 A | 8/1990 | Eggers | |
| D311,061 S | 10/1990 | Vrana et al. | |
| 4,976,685 A | 12/1990 | Block, Jr. | |
| 4,997,464 A | 3/1991 | Kopf | |
| 5,047,147 A | 9/1991 | Chevallet et al. | |
| 5,049,492 A | 9/1991 | Sauer et al. | |
| 5,059,173 A | 10/1991 | Sacco | |
| 5,061,236 A | 10/1991 | Sutherland et al. | |
| 5,061,365 A | 10/1991 | Utterberg | |
| 5,112,480 A | 5/1992 | Hukasawa | |
| 5,167,921 A | 12/1992 | Gordon | |
| 5,178,763 A | 1/1993 | Delaunay | |
| 5,204,000 A | 4/1993 | Steadman et al. | |
| 5,228,889 A | 7/1993 | Cortial et al. | |
| 5,246,560 A | 9/1993 | Nekoksa et al. | |
| 5,268,077 A | 12/1993 | Bubik et al. | |
| 5,328,461 A | 7/1994 | Utterberg | |
| 5,356,376 A | 10/1994 | Milijasevic et al. | |
| 5,358,481 A | 10/1994 | Todd et al. | |
| 5,368,555 A | 11/1994 | Sussman et al. | |
| 5,394,732 A | 3/1995 | Johnson et al. | |
| 5,411,705 A | 5/1995 | Thor et al. | |
| 5,421,815 A | 6/1995 | Noguchi et al. | |
| 5,429,595 A | 7/1995 | Wright, Jr. et al. | |
| 5,441,636 A | 8/1995 | Chevallet et al. | |
| 5,468,388 A | 11/1995 | Goddard et al. | |
| 5,489,385 A | 2/1996 | Raabe et al. | |
| 5,503,801 A | 4/1996 | Brugger | |
| 5,509,895 A | 4/1996 | Noguchi et al. | |
| 5,520,640 A | 5/1996 | Utterberg | |
| 5,578,070 A | 11/1996 | Utterberg | |
| 5,591,251 A | 1/1997 | Brugger | |
| 5,605,540 A | 2/1997 | Utterberg | |
| 5,637,081 A | 6/1997 | Noguchi et al. | |
| 5,643,250 A | 7/1997 | Utterberg | |
| 5,650,071 A | 7/1997 | Brugger et al. | |
| 5,674,199 A | 10/1997 | Brugger | |
| 5,681,294 A | 10/1997 | Osborne et al. | |
| 5,683,355 A | 11/1997 | Fini et al. | |
| 5,730,730 A | 3/1998 | Darling, Jr. | |
| 5,763,266 A | 6/1998 | Palsson et al. | |
| 5,776,091 A | 7/1998 | Brugger et al. | |
| 5,800,597 A | 9/1998 | Perrotta et al. | |
| 5,830,185 A | 11/1998 | Block, Jr. | |
| 5,849,065 A | 12/1998 | Wojke | |
| 5,851,202 A | 12/1998 | Carlsson | |
| 5,858,239 A | 1/1999 | Kenley et al. | |
| 5,863,421 A | 1/1999 | Peter, Jr. et al. | |
| 5,895,368 A | 4/1999 | Utterberg | |
| 5,928,889 A | 7/1999 | Bakich et al. | |
| 5,931,990 A | 8/1999 | Andrews | |
| 5,951,870 A | 9/1999 | Utterberg | |
| 5,980,741 A | 11/1999 | Schnell et al. | |
| 5,983,947 A | 11/1999 | Utterberg | |
| 5,989,318 A | 11/1999 | Schroll | |
| 6,010,623 A | 1/2000 | Schnell et al. | |
| 6,019,824 A | 2/2000 | Schnell | |
| 6,046,806 A | 4/2000 | Thompson | |
| 6,051,134 A | 4/2000 | Schnell et al. | |
| 6,053,967 A | 4/2000 | Heilmann et al. | |
| 6,066,111 A | 5/2000 | Brockhoff | |
| 6,071,269 A | 6/2000 | Schnell et al. | |
| 6,117,342 A | 9/2000 | Schnell et al. | |
| 6,171,484 B1 | 1/2001 | Schnell et al. | |
| 6,176,903 B1 | 1/2001 | Wamsiedler | |
| 6,187,198 B1 | 2/2001 | Utterberg | |
| 6,206,954 B1 | 3/2001 | Schnell et al. | |
| 6,251,167 B1 | 6/2001 | Berson | |
| 6,312,414 B1 | 11/2001 | Brockhoff et al. | |
| 6,344,139 B1 | 2/2002 | Utterberg | |
| 6,357,600 B1 | 3/2002 | Scagliarini | |
| 6,391,541 B1 | 5/2002 | Petersen et al. | |
| 6,391,638 B1 | 5/2002 | Shaaltiel | |
| 6,464,878 B2 | 10/2002 | Utterberg | |
| 6,481,455 B2 | 11/2002 | Gustafson et al. | |
| 6,514,255 B1 | 2/2003 | Ferree | |
| 6,537,356 B1 | 3/2003 | Soriano | |
| 6,562,107 B2 | 5/2003 | Purdom et al. | |
| 6,755,801 B2 | 6/2004 | Utterberg et al. | |
| 6,827,862 B1 | 12/2004 | Brockhoff et al. | |
| 2001/0042441 A1 | 11/2001 | Purdom et al. | |
| 2002/0091350 A1 * | 7/2002 | Belson | 604/5.04 |
| 2004/0019312 A1 | 1/2004 | Childers et al. | |
| 2004/0019313 A1 | 1/2004 | Childers et al. | |
| 2005/0247203 A1 | 11/2005 | Chevallet et al. | |
| 2006/0137663 A1 | 6/2006 | Vaught | |

FOREIGN PATENT DOCUMENTS

| | | |
|---|---|---|
| DE | 1806654 | 5/1970 |
| DE | 102005060846 | 6/2007 |
| EP | 0 058 325 | 8/1982 |
| EP | 0 106 026 | 4/1984 |
| EP | 0 143 340 | 6/1985 |
| EP | 0 318 993 | 6/1989 |
| EP | 0 350 675 | 1/1990 |
| EP | 0 501 144 | 1/1992 |
| EP | 0 587 251 | 3/1994 |
| EP | 0 776 222 | 4/2003 |
| GB | 1 408 319 | 10/1975 |
| GB | 1 554 810 | 10/1979 |
| GB | 2 061 755 | 5/1981 |
| GB | 2 212 739 | 8/1989 |
| WO | WO 98/23353 | 6/1998 |
| WO | PCT/US08/068028 | 10/2008 |

* cited by examiner

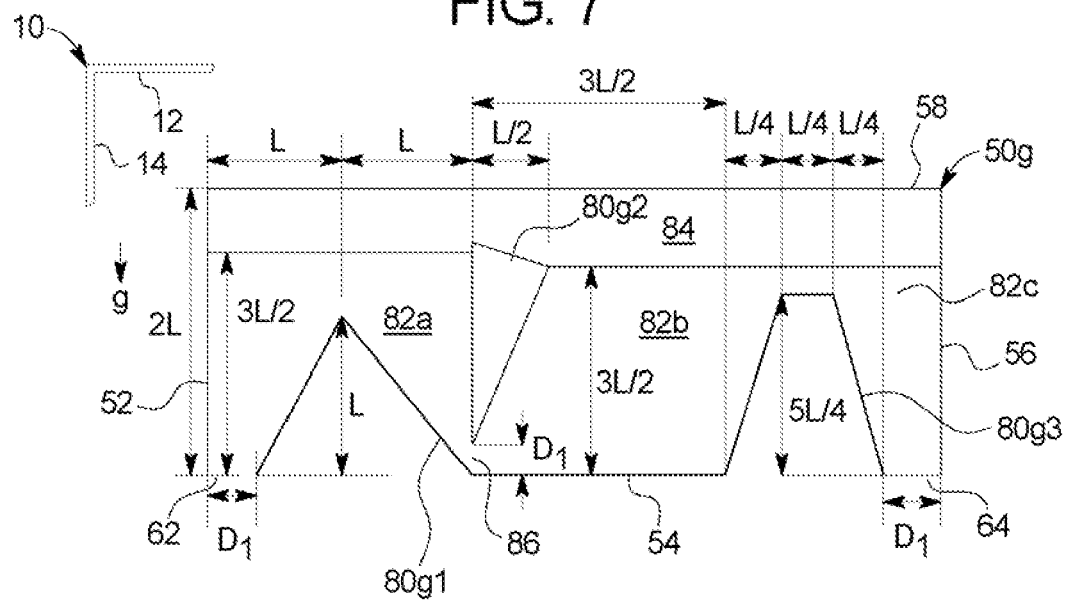
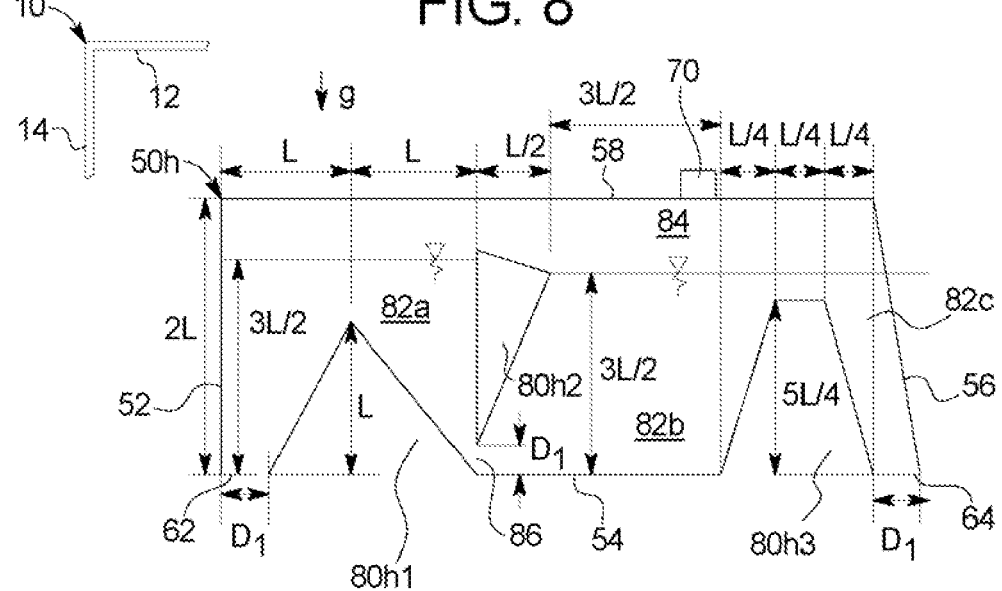

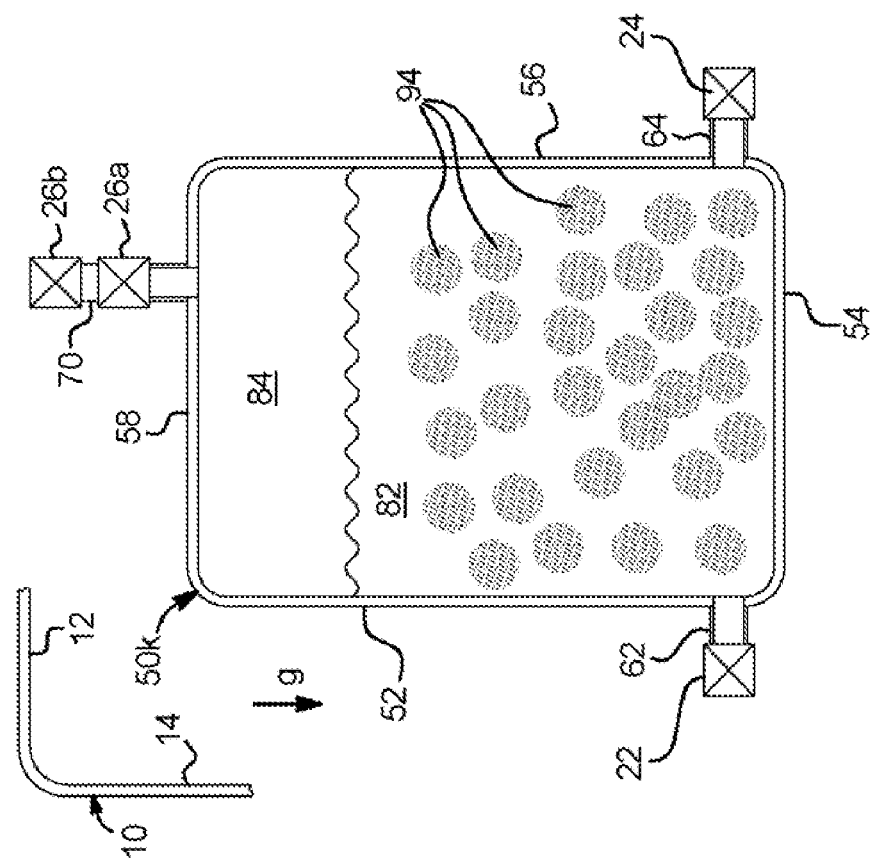
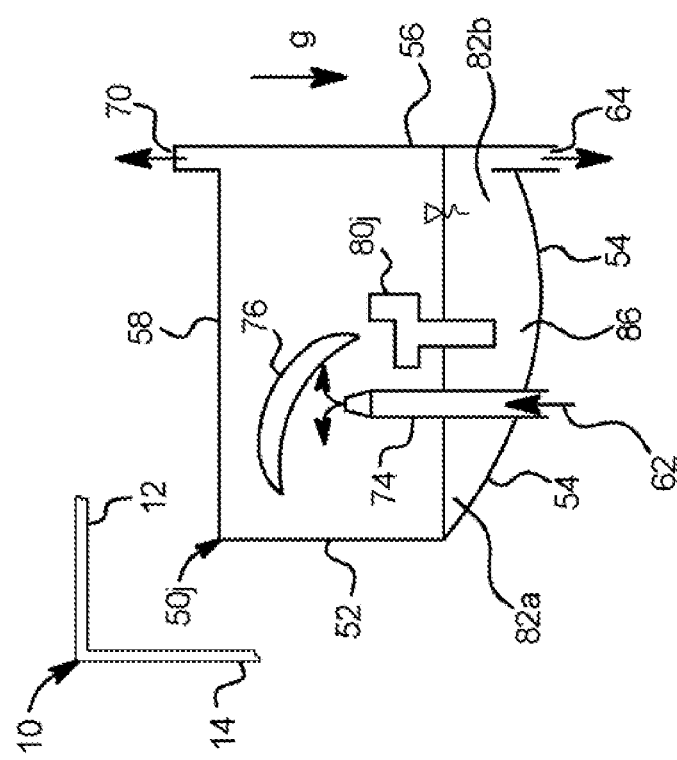

FLUID DELIVERY SYSTEMS AND METHODS HAVING FLOATING BAFFLE AIDED AIR REMOVAL

PRIORITY

This application claims priority to and the benefit as a divisional application of U.S. patent application entitled, "Dialysis Systems Having Air Traps With Internal Structures To Enhance Air Removal", Ser. No. 11/865,577, filed Oct. 1, 2007, the entire contents of which are incorporated herein by reference and relied upon.

BACKGROUND

The examples discussed below relate generally to medical fluid delivery. More particularly, the examples disclose systems, methods and apparatuses for dialysis such as hemodialysis ("HD") automated peritoneal dialysis ("APD").

Due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate to cause diffusion. Hemofiltration ("HF") is an alternative renal replacement therapy that relies on a convective transport of toxins from patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that a patient receiving more frequent treatments removes more toxins and waste products than a patient receiving less frequent but perhaps longer treatments. A patient receiving more frequent treatments does not experience as much of a down cycle as does an in-center patient who has built-up two or three days worth of toxins prior to a treatment. In certain areas, the closest dialysis center can be many miles from the patient's home causing door-to-door treatment time to consume a large portion of the day. HHD can take place overnight or during the day while the patient relaxes, works or is otherwise productive.

Another type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. Osmotic agent in dialysis provides the osmotic gradient. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain to allow spent dialysate fluid to drain from the peritoneal cavity. The patient then connects the catheter to a bag of fresh dialysate to infuse fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter and into the patient's peritoneal cavity. APD machines also allow for the dialysate to dwell within the cavity and for the transfer of waste, toxins and excess water to take place. The source can include multiple sterile dialysate solution bags.

APD machines pump spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In any of the above modalities, entrained air and other gases are a concern. Entrained air can cause inaccuracies when pumping dialysate for either PD or HD. Entrained air can cause a reduction in effective surface area in a hemodialysis filter when it accumulates on the filter fibers, leading to a reduction in the effectiveness of the therapy. Entrained air entering a patient's peritoneum during PD can cause discomfort. Entrained air entering a patient's bloodstream during HD can have severe consequences. Accordingly, a need exists to provide an apparatus that ensures that entrained air is removed from dialysate or blood prior to delivering such fluids to the patient.

SUMMARY

The present disclosure relates to air and gas removal for dialysis systems and extracorporeal devices, e.g., blood separation, blood warming, etc. The structures disclosed herein can be performed in any type of peritoneal dialysis treatment or blood dialysis treatment such as hemodialysis, hemofiltration, hemodiafiltration and continuous renal replacement therapy. The embodiments below are disclosed in connection with a dialysis cassette that is loaded into a dialysis instrument. The dialysis cassette is part of an overall dialysis set which can include one or more supply bag, or connection to the dialysate generation system, one or more drain bag, a heater bag and associated tubing connecting the bags to the dialysis cassette. The user places the dialysis cassette within the dialysis instrument for therapy. The dialysis cassette can include one or more pump chamber, flow path and/or valve chamber. The dialysis instrument includes one or more pump actuator that actuates the pump chamber of the disposable cassette. The dialysis instrument also includes one or more valve actuator that actuates the valve chamber of the disposable cassette. The disposable cassette can also include a fluid heating pathway that operates with a fluid heater of the dialysis instrument. The disposable cassette can also include various regions for sensing pressure, fluid composition, fluid temperature, and fluid levels.

While air traps 50 are shown herein in connection with a disposable set described below, the separation chambers are alternatively stand-alone apparatuses that operate independent of the disposable cassette. Further, the present disclosure mainly discusses air but other gases can also be present and therefore the present air separation chambers can also trap these gases. In PD for example, gases from the patient can become entrained in fluid being pumped form the system. Also, gases from dialysate concentrate, such as bicarbonate can become entrained in fresh dialysate. It is expressly contemplated for the air separation chambers of the present disclosure to remove these additional types of gases.

As mentioned above, air in dialysate or dialysis fluid as well as air in blood needs to be removed before any of these fluids are either delivered to a dialyzer or patient. Air can be present in the system via air trapped in supply bags, air trapped in the tubes leading from the supply bags to the disposable cassette, air not completely primed from the disposable cassette itself and air that is released from solution when the dialysis fluid is mixed and/or heated. Air can also signal a leak in the disposable unit.

The air traps discussed below are shown generally in connection with a dialysis fluid, such as dialysate, having entrained air. It should be appreciated however that the embodiments are applicable equally to the removal of air from blood pumped from a patient to a hemodialyzer or hemofilter. As used herein, the term dialysis fluid includes, without limitation, mixed dialysate, mixed infusate, mixed replacement fluid, concentrated components of any of these, and blood.

In one embodiment, the disposable cassette defines an air separation chamber that has a fluid inlet and a fluid outlet. An inlet valve and an outlet valve are paired with the fluid inlet and fluid outlet of the air separation chamber, respectively. The air separation chamber also includes an air vent outlet, which is in fluid communication with one or more air vent valve. The air removed from fluid in the air trap is sent to atmosphere, to a holding vessel such as an empty bag or a fluid filled bag (e.g, saline bag or dialysate bag), or to a drain, for example, whichever is desired.

In one embodiment, the air separation chamber is configured with respect to the other components of the disposable cassette such that when the cassette is loaded into the dialysis instrument, the fluid inlet and fluid outlet are located towards a bottom or bottom wall of the air separation chamber, while the air outlet is located at or near the top of the dialysis instrument. Such configuration allows buoyancy forces to lift air bubbles from the dialysis fluid to the top of the air separation chamber for venting.

The dialysis cassette in one embodiment includes a rigid portion, which can be a hard plastic. The rigid portion is formed to have pump chambers (e.g., for diaphragm pumps) or pump tubing (for peristaltic pumping), fluid pathways and valve chambers. The rigid portion also defines some or all of the air separation chamber. It is contemplated that the disposable cassette will have flexible sheeting welded to one or both sides of the rigid portion of the cassette. The flexible sheeting allows a pneumatic or mechanical force to be applied to the pump chambers (e.g., diaphragm) and valve chambers to operate those chambers. It is also contemplated that at least one outer surface of the air separation chamber consumes a portion of one or both flexible sheets. In addition, one or both sides of the dialysis cassette can be rigid.

The disposable cassette can have a base wall or mid-plane that divides the disposable cassette into first and second sides. For example, in one embodiment the flow paths are provided on one side of the disposable cassette (one side of the base wall), while the pump and valve chambers are provided on the other side of the disposable cassette. The air separation chamber in one embodiment is provided on either the first or second side, whichever is more convenient. Here, the air separation chamber has one side surface that is a rigid mid-plane and a second side surface that is cassette sheeting. The cassette sheeting is welded to an air separation chamber inlet wall, an air separation chamber outlet wall, an air separation chamber top wall and an air separation chamber bottom wall, which each extends from and is formed with the mid-plane of the rigid portion.

It is expressly contemplated however to make the outer wall of the disposable cassette from a rigid material rather than from cassette sheeting. For example, a rigid piece could be welded, adhered or otherwise sealingly bonded to the air separation walls extending from the mid-plane of the rigid portion, or could be formed as one piece along with the mid-plane of the rigid portion during manufacture.

In still a further alternative embodiment, the mid-plane is not present within the air separation chamber, but the air separation chamber is bonded on two-sides by flexible sheeting. Still further alternatively, the mid-plane is not provided, however, the outer walls of the air separation chamber are rigid and adhere to the top, bottom, inlet and outlet walls via a suitable sealing process.

The air separation chamber includes one or more baffle or separation wall that is configured to disrupt the flow of fluid through the air separation chamber, promoting the separation of air from the dialysis fluid. In one embodiment, the baffle or separation wall is a single wall formed of the rigid material and extending upward from a base wall of the air separation chamber. The single baffle wall can be parallel to the inlet and outlet walls. Alternatively, the baffle is angled relative to one or both the inlet and outlet air chamber walls. The inlet and outlet air chamber walls can themselves be squared with the side walls of the disposable cassette. Alternatively, the inlet and outlet air separation chamber walls are angled with respect to the cassette side walls. For example, the air separation chamber can form a parallelogram shape with the inlet and outlet walls at a nonorthogonal angle with respect to the top and bottom walls of the air separation chamber. The baffle can be angled the same as or different than the inlet and outlet walls.

In one embodiment, inlet and outlet pathways leading to and from the air separation chamber inlet and outlet are inline with each other and are disposed at least substantially perpendicular to an air vent pathway leading out of the top of the disposable cassette. Here, the inlet and outlet pathways can be at least substantially horizontally disposed when the disposable cassette is loaded into the dialysis instrument. Alternatively, the inlet and outlet pathways are not aligned with each other and are provided at a non-horizontal angle. Indeed, in one embodiment, the inlet and outlet pathways are at least substantially vertically disposed and parallel to the air vent pathway when the cassette is loaded for operation.

The baffle is not limited to being a single plate and can instead be a polygonal shape formed from one or more wall extending within the air separation chamber. For example, the polygonal shape can have a wall that includes a straight or nonlinear surface. The nonlinear surface can extend from the bottom wall of the air chamber upwardly towards the air vent, change direction towards the outlet of the air chamber and then extend downwardly to the bottom wall of the air separation chamber. The polygonal baffle removes a volume within the air separation chamber such that the volume is separated from the dialysis fluid. The removed volume can be a solid rigid material or can be a hollow volume beneath the baffle wall.

The surface of the polygonal baffle forces the fluid to change direction at least once between the dialysis fluid inlet and the dialysis fluid outlet of the air separation chamber. The polygonal shape of the baffle can have one or more straight side so as to form a triangle or rectangle within the air separation chamber. The polygonal shape can be curved so as to form a semicircle within the air separation chamber. Further alternatively, the polygonal shape can have a combination of straight and curved surfaces.

While many of the embodiments below show the single wall or polygonal baffle extending from the bottom wall of the air separation chamber, it is expressly contemplated to extend the baffle from a wall different from the bottom wall. The baffle can instead be located above the bottom wall and extend for example from the mid-plane of the rigid portion. This baffle can also be a single wall baffle or a polygonal baffle having multiple walls or a single continuous wall. The baffle an be utilized as a barrier which forces the fluid to overflow or creates a constriction between another structural feature such that the fluid is forced to flow through.

It is further contemplated to provide multiple baffles within the air separation chamber. The multiple baffles can be any combination of single wall, polygonal shape, attached to or not attached to the bottom wall, and perpendicular or angled with respect to the dialysate inlet and outlet. A second baffle can for example extend from a surface of the first baffle. For example, a second single wall baffle can extend from a first polygonal baffle. Further alternatively, multiple single wall baffles can extend from the same polygonal baffle or from different polygonal baffles.

In still a further alternative embodiment, the baffle is configured to float within the air separation chamber. That is, the baffle is not connected to any of the walls of the rigid portion of the disposable cassette and instead is moveable independently within the air separation chamber. For example, the air separation chamber can include a plurality of spheres or other shaped members, which are too large to fit through any of the dialysate inlet, dialysis fluid outlet or air chamber openings. The plural spheres provide increased surface contact area with the fluid to better remove air bubbles from the liquid. Additionally, the free motion accorded to the baffle (or plurality of baffles) allows their portion to disrupt air bubbles that may have accumulated through surface tension onto various surfaces within the chamber or on themselves. This disruption allows the bubbles to be coalesced into larger bubbles and carried to the air/fluid interface of the chamber for venting. Alternatively, a loose fitting geometry, such as a coiled or twisted strip of plastic, is moveable within the air separation chamber to provide a large contact surface area with the dialysis fluid and to route fluid towards the air/fluid interface of the chamber where bubbles can be separated from the fluid. To this end, the spheres or other shaped members can be textured to provide even additional surface contact area. In an alternate stationary geometry, the geometry can be rigid on the air trap.

It is further contemplated to provide a nozzle at the air separation chamber inlet, which causes the inlet dialysis fluid to form a spray or mist, which further aids in removing air from the dialysis fluid. Still further, it is contemplated to provide a vibrator, such as an ultrasonic or mechanical vibrator within the disposable cassette, which contacts a portion of the disposable set, such as a portion of the disposable cassette. The vibrator vibrates the disposable cassette to further aid in dislodging air bubbles from the dialysis stream and to aid in their coalescence that increases the bubbles' buoyancy force, thereby inducing them to float to the surface of the chamber for venting. In an embodiment, the ultrasonic or other type of vibrator is positioned within the dialysis instrument to contact the disposable cassette at the air separation chamber. The vibrator provides a force in addition to buoyancy to separate air from the fluid, forming an air separation area. The air separation area attacks entrained air on multiple fronts, one using the above described baffles and another using the ultrasonic or other type of vibration. It is further contemplated to add the nozzle at the inlet to this two-pronged air separation attack to form a three-pronged attack.

It is accordingly an advantage of the present disclosure to provide improved air separation chambers for the removal of air from the dialysis fluid or blood flowing through a disposable dialysis fluid apparatus.

Additional features and advantages are described herein, and will be apparent from, the following Detailed Description and the figures.

BRIEF DESCRIPTION OF THE FIGURES

FIG. 7 is yet a further elevation view of one embodiment of a dialysis fluid air trap of the present disclosure.

FIG. 8 is an eighth elevation view of one embodiment of a dialysis fluid air trap of the present disclosure.

FIG. 11 is a tenth elevation view of one embodiment of a dialysis fluid air trap of the present disclosure.

FIG. 12 is an eleventh elevation view of one embodiment of a dialysis fluid air trap of the present disclosure.

DETAILED DESCRIPTION

Figure 1:
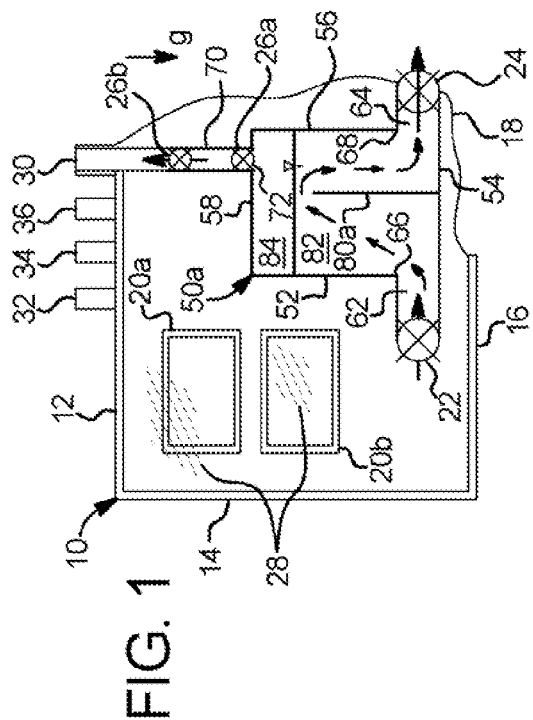
FIG. 1 is one elevation view of one embodiment of a dialysis fluid air trap of the present disclosure.

Referring now to the drawings and in particular to FIG. 1, dialysis cassette 10 having air trap 50 illustrates one embodiment of the present disclosure. Dialysis cassette 10 is operable with any type of dialysis instrument, such as a peritoneal dialysis instrument, hemodialysis, hemofiltration, hemodiafiltration or continuous renal replacement therapy instrument. Dialysis cassette 10 can hold a dialysis fluid, such as dialysate or blood. The dialysis fluid can be premixed or cassette 10 can carry a component of dialysate such as a dialysate concentrate.

Dialysis cassette 10 in one embodiment is part of a disposable set, which includes one or more supply bag, a drain bag, a heater bag, and tubing running from those bags (not illustrated) to dialysis cassette 10. Dialysis cassette 10 in one embodiment is disposable, however, dialysis cassette 10 could be cleaned for multiple uses in which case the air traps described herein are used multiple times. Dialysis cassette 10 includes a rigid portion have a cassette top wall 12, a cassette side wall 14 and a cassette bottom wall 16. Suitable materials for the rigid portion include polyvinyl chloride ("PVC"), acrylic, ABS, polycarbonate, and polyolefin blends. The rigid portion of cassette 10 also includes a base wall or mid-plane 18, which separates cassette 10 into first and second sides.

The side of mid-plane 18 illustrated in FIG. 1 includes pump chambers 20a and 20b, which here are part of a pneumatically and/or electromechanically operated diaphragm pump. Alternatively, cassette 10 includes peristaltic pumping tubes that operate with a peristaltic pump actuator of the dialysis instrument. Cassette 10 also includes valve chambers, such as air separation chamber inlet valve chamber 22, air separation chamber outlet valve chamber 24 and air separation chamber air vent valve chambers 26a and 26b. The valve chambers can also be pneumatically and/or electromechanically operated.

The other side of cassette 10, which is divided by mid-plane 18 (not illustrated), can include flow paths and/or other valve chambers and/or pump chambers. It should be appreciated that cassette 10 can have different structural layouts without affecting the performance air separation chamber 50. Air separation chamber 50 can be located on either side of mid-plane 18 for space purposes or for other reasons related to component layout.

In the illustrated embodiment, the rigid portion of cassette 10 defines the wall or walls of pump chambers 20a and 20b, which in the illustrated embodiment operate with a flexible cassette sheeting 28, which is welded, heat sealed or solvent bonded to rigid walls 12, 14, 16, etc., of the rigid portion of cassette 10. Suitable cassette sheeting 28 includes polyvinyl chloride ("PVC"), polypropylene/polyethylene blends, polypropylene or Kraton blends, polyester, polyolefin, and ULDPE. The suitable PVC sheeting can include, for example, monolayer PVC films, non-DEHP PVC monolayer films, monolayer non-PVC and multilayer non-PVC films (wherein different layers are chosen to provide strength, weldability, abrasion resistance and minimal "sticktion" to other materials such as rigid cassette materials). Multiple layers can be coextruded or laminated with or without a gas barrier.

Cassette sheeting 28 is also used to open and close valve chambers, such as chambers 22, 24, 26a and 26b. The dialysis instrument includes a controller unit that operates a program that controls when valves 22, 24, 26a and 26b are opened or closed. The controller unit can include, but is not limited to, a processor, memory, hardware (e.g. sensors, actuators, I/O boards, etc.), software, and algorithms. For example, inlet and outlet valves 22 and 24 can be sequenced during priming to fill the air separation chamber. Inlet and outlet valves 22 and 24 are open during dialysis fluid delivery and/or blood pumping to remove air from those fluids. While inlet and outlet valves 22 and 24 are shown directly in front of and behind the air separation chambers, it is also contemplated to move one or both the inlet and outlet valves 22 and 24 further away from the air separation chamber. One or both of inlet and outlet valves 22 and 24 can be configured to control flow to multiple places within cassette 10, including the air separation chamber.

The controller unit is also programmed to operate vent valves 26a and 26b so as to remove air from the air separation chamber in a manner so as not to effect the sterility of the dialysis fluid flowing through cassette 10. To this end, the controller unit can operate with a signal from an optical or ultrasonic sensor monitoring the level of fluid within the air separation chamber. Alternatively, the controller unit can operate with an air pressure signal from a pressure sensor monitoring the pressure of air in the chamber. In either case, the signal is monitored to determine when to perform the air purge valve sequence of valves 26a and 26b. Alternatively, the controller unit is programmed to perform the valve sequence for valves 26a and 26b at set intervals.

Cassette 10 in FIG. 1 also includes a plurality of rigid ports extending from one of the walls, such as cassette top wall 12. In the illustrated embodiment, cassette 10 includes a vent port 30, which operates with vent valves 26a and 26b and air separation chamber 50. Cassette 10 also includes other ports, such as one or more fluid supply port 32, a drain port 34, a to- or from-heater port 36 and other ports, such as a patient port and a heater bag port.

Vent port 30 can vent air from air separation chamber 50 to atmosphere or to drain in different embodiments. Cassette 10 can include other apparatuses (not illustrated), such as pressure sensing areas, heater flow path areas, and additional pumping areas, such as heparin and/or saline pumping areas.

Air trap 50 refers generally to each of the air traps 50a to 50l discussed herein. FIG. 1 shows one embodiment of the air separation chamber or air trap of the present disclosure, namely, air separation chamber 50a. Air separation chamber 50a includes an inlet wall 52, a bottom wall 54, an outlet wall 56 and a top wall 58. Walls 52 to 58 can extend from mid-plane 18, such that mid-plane 18 forms one of the broad sides of air separation chamber 50. Alternatively, mid-plane 18 extends along the outside of walls 52 to 58 but not inside air separation 50, such that walls 52 to 58 extend the entire thickness of cassette 10. Here, both broad surfaces of air separation chamber 50 can be made of flexible sheeting 28.

Alternatively, one or both of the broad surfaces of air separation chamber 50 are made of the rigid material, wherein sheeting 28 is welded to the broad surfaces of air separation chamber 50. For example, the profile shape of air separation chamber 50 can be welded or solvent bonded to walls 52 to 58. Thereafter, the sheeting is welded or solvent bonded to the edges of the rigid broad sides of air separation chamber 50.

In the case where mid-plane 18 forms one of the broad sides of air separation chamber 50, the outer broad surface of air separation 50 can be flexible sheet 28 or a rigid piece, welded or solvent bonded to walls 52 to 58.

Inlet valve 22 opens or closes an inlet pathway 62, while outlet valve 24 opens or closes an outlet pathway 64. Inlet pathway 62 communicates with air separation chamber 50 via inlet 66, which is formed in wall 52 of air chamber 50. Outlet pathway 64 communicates with air separation chamber 50 via an outlet 68 formed in wall 56 of air separation chamber 50. It should be appreciated that while valves 22 and 24 are shown as inlet and outlet valves, respectively, each valve can be either an inlet or an outlet valve, e.g., for priming purposes both valves 22 and 24 may be inlet valves that prime fill chamber 50a up to a predetermined fluid level within the chamber.

Vent valves 26a and 26b open and close a vent line 70. Vent 70 communicates with vent port 30 and with air separation chamber 50 via a vent outlet 72 formed in top wall 58 of air separation chamber 50. Dual vent valves 26a and 26b allow the controller unit of the dialysis instrument to isolate a slug of air in vent line 70 before vent valve 26b is opened, allowing the air to escape via vent port 30 to atmosphere or drain. In the programmed sequence, with vent valve 26b closed, vent valve 26a is opened allowing vent line 70 to become pressurized with air. Once line 70 becomes pressurized, valve 26a is closed and valve 26b is opened, relieving the pressure in vent line 70.

With air separation chamber 50a, inlet pathway 62 and outlet pathway 64 are aligned with each other and are at least substantially perpendicular to vent line 70. Walls 52 and 56 are at least substantially orthogonal to walls 54 and 58, forming a square or rectangular air separation chamber 50.

Air separation chamber 50a includes a single baffle 80a, which as illustrated is a single wall extending vertically upwardly from bottom wall 54 past inlet 62 and outlet 64. Single baffle 80a is also integral with mid-plane 18 in one embodiment. Baffle 80a forces the flow of dialysis fluid 82 vertically upward from inlet 62 against the direction of gravity g, along a first surface of baffle wall 80a. Baffle 80a and outlet wall 56 then force dialysis fluid 82 down a return surface of baffle wall 80a, to outlet flow path 64 and to outlet valve 24. As the flow of dialysis fluid 82 rises and flows over separation wall or baffle 80a, the fluid it is slowed down due to increased cross-sectional area of air chamber 50a. Air is collected in the upper section 84 of chamber 50a. The primary purging action of air chamber 50a is the force of buoyancy.

Figure 2:
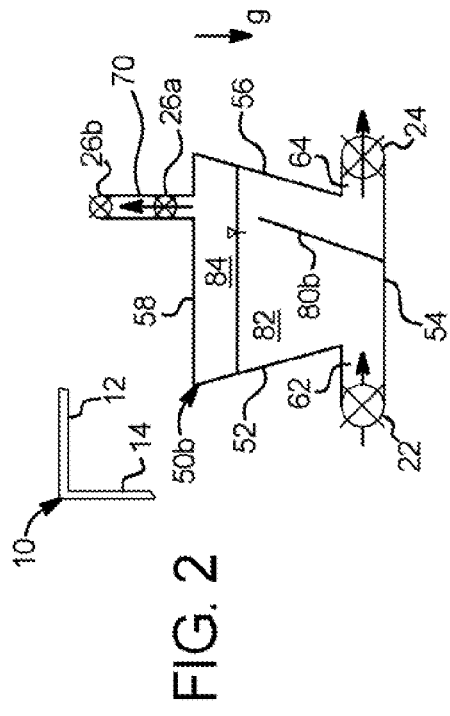
FIG. 2 is another elevation view of one embodiment of a dialysis fluid air trap of the present disclosure.

Referring now to FIG. 2, air separation chamber 50b operable with cassette 10 includes many of the same features as air separation chamber 50a. Here however, inlet wall 52 and outlet wall 56 are tapered outwardly from bottom wall 54 to top wall 58, producing an air separation chamber having a substantially trapezoidal shape. The shape of air separation chamber 50b causes the dialysis fluid 82 flow cross-section to increase gradually in a vertical direction, enabling further slowing of the fluid, and allowing more time for buoyancy forces to lift air bubbles from the dialysis fluid 82.

Single wall baffle 80b in air separation chamber 50b is tilted away from the 90° vertical position of baffle 80a, towards outlet line 64 and outlet valve 24. Tilted baffle 80b causes the cross-section of dialysis fluid flow 82 on the inlet side of chamber 50b to increase even more as dialysis fluid 82 flows vertically upward until reaching the free end of baffle 80b, further slowing the fluid and allowing more time for buoyancy forces to lift air bubbles from the dialysis fluid 82.

Single wall baffles 80a and 80b and indeed any of the single wall baffles describe herein (baffles 80) extend in one embodiment the total thickness of the air separation chamber, for example, all the way from mid-plane 18 to the cassette sheeting 28. Alternatively, wall or baffle 80 does not extend all the way across the width of the air separation chamber. In such case, additional gusseting or support can be provided. Also, additional support or gusseting can be provided to baffles 80 when the air separation chamber is bounded on both broad sides by flexible sheeting 28.

Figure 3:
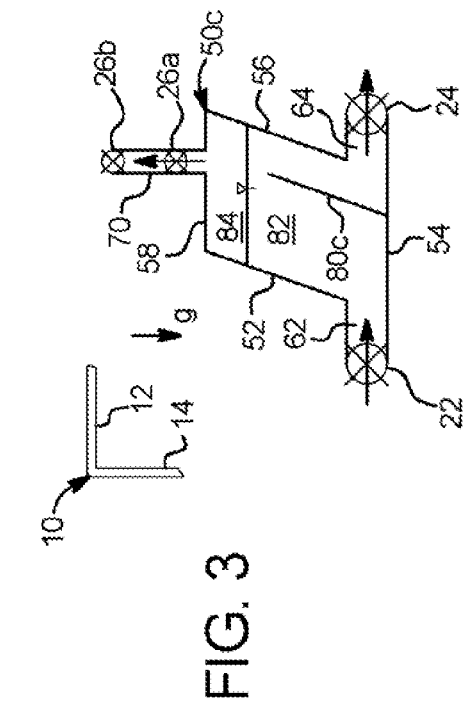
FIG. 3 is further elevation view of one embodiment of a dialysis fluid air trap of the present disclosure.

FIG. 3 illustrates a further alternative air separation chamber 50c operable with cassette 10, in which inlet wall 52 and outlet wall 56 are positioned at a non-orthogonal angle with respect to bottom wall 54 and top wall 58. The shape of air trap 50c is substantially that of a parallelogram. Baffle 80c is at least substantially the same as baffle 80b and is at least substantially aligned with the angled walls 52 and 56 in air separation chamber 50c. Besides increasing cross-sectional flow area on the inlet side of baffles 80b and 80c, angling baffles 80b and 80c in the direction shown also extends or lengthens the dialysis fluid 82 flow path along the left or inlet portion of the air separation chamber 50a.

Figure 4:
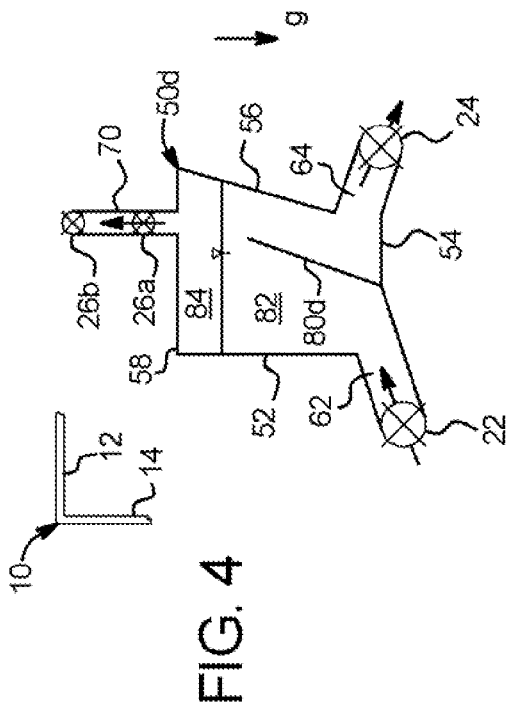
FIG. 4 is still another elevation view of one embodiment of a dialysis fluid air trap of the present disclosure.

Air separation chamber 50d of FIG. 4 operable with cassette 10 illustrates that inlet path 62 and outlet path 64 are not aligned and are not orthogonal to vent line 70. The shape of air trap 50d is once again polygonal. Angled baffle 80d is the same as or similar to baffles 80b and 80c. However, as illustrated in FIG. 4, the direction of the inlet and outlet pathways, 62 and 64 respectively, can be in directions other than horizontal or vertical. Air separation chamber 50d allows a cross-sectional area on the inlet portion of the valve chamber to increase, such that fluid velocity slows as it fills over baffle 80d. Outlet flowpath 64 angled as shown tends to lengthen the exit flow path, between baffle 80d and outlet wall 56, of chamber 50d since in this configuration buoyancy and drag forces acting on the air bubbles are not in opposite directions. The buoyancy force is always opposite to the direction of gravity whereas the drag force is opposite the velocity of a particle. The bubbles would rise up and they will only feel a smaller component of the drag force opposing their rise.

Figure 5:
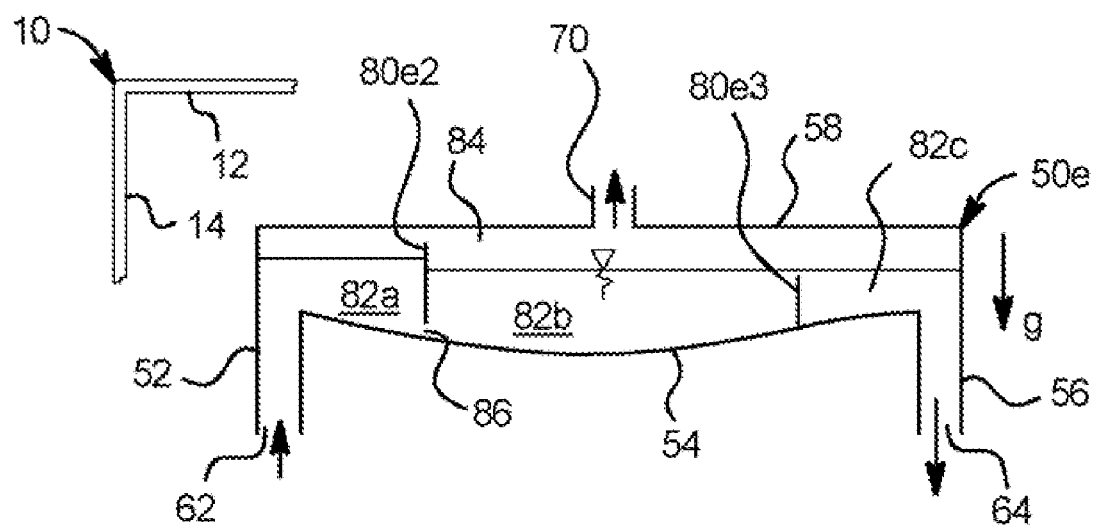
FIG. 5 is still a further elevation view of one embodiment of a dialysis fluid air trap of the present disclosure.

Air separation chamber 50e of FIG. 5 operable with cassette 10 illustrates a number of additional concepts. Here, inlet and outlet pathways 62 and 64 are vertical when cassette 10 is placed in an operable position. Dialysis fluid flow 82 in pathways 62 and 64 is accordingly aided or impeded by the force of gravity g.

Air separation chamber 50e also has multiple baffles 80e2 and 80e3. Bottom wall 54 includes or has multiple surfaces or walls which force dialysis fluid 82 upwardly through inlet pathway 62, over a curved or nonlinear portion of bottom wall 54, down a vertical wall of bottom wall 54, and out outlet pathway 64. Air separation chamber 50e includes first and second flow restrictions or baffles 80e2 and 80e3. Baffle 80e2 is not connected to bottom wall 54 and instead extends from mid-plane 18. Baffle 80e2 forms a narrow channel 86 between the baffle and the top surface of bottom wall 54. Dialysis fluid flow 82 is forced through channel 86. Second baffle 80e3 extends from bottom wall 54 and thus forces fluid to flow up over bottom wall 54.

The net effect of the two baffles 80e2 and 80e3 of air separation chamber 50e is the creation, essentially, of three fluid regions 82a, 82b and 82c of dialysis fluid 82 within the air separation chamber. Each region resides above the curved surface of bottom wall 54. In the regions, dialysis fluid 82 flows into chamber 50e through inlet pathway 62 and into left chamber 82a. Baffle 80e2 forces fluid to flow through a constriction 86 into middle region 82b. Fluid velocity in region 82a decreases due to the restriction through opening to 84, aiding de-gassing due to buoyancy force. Fluid pressure builds in region 82a and a difference in fluid level as illustrated results between regions 82a and 82b.

Dialysis fluid 82 rises for a second time in large region 82b, resulting in a slowed flow and a second opportunity to de-gas via buoyancy forces. When the dialysis fluid level rises in region 82b to the free end of second baffle 80e3, the dialysis fluid 82 flows over baffle 80e3 and begins to fill third region 82c. The surface of baffle 80e1 is channeled slightly to allow the dialysis fluid 82 to pool in both regions 82b and 82c while filling. Dialysis fluid 82 rises to the edge of outlet pathway 64 and then flows out pathway 64, leaving air separation chamber 50e. Depending on the dialysis fluid 82 flowrate into region 82c, the fluid level in the region may be the same as (as shown) or lower than that of 82b. Region 82c aids in de-gassing any air bubbles remaining in dialysis fluid 82.

Figure 6:
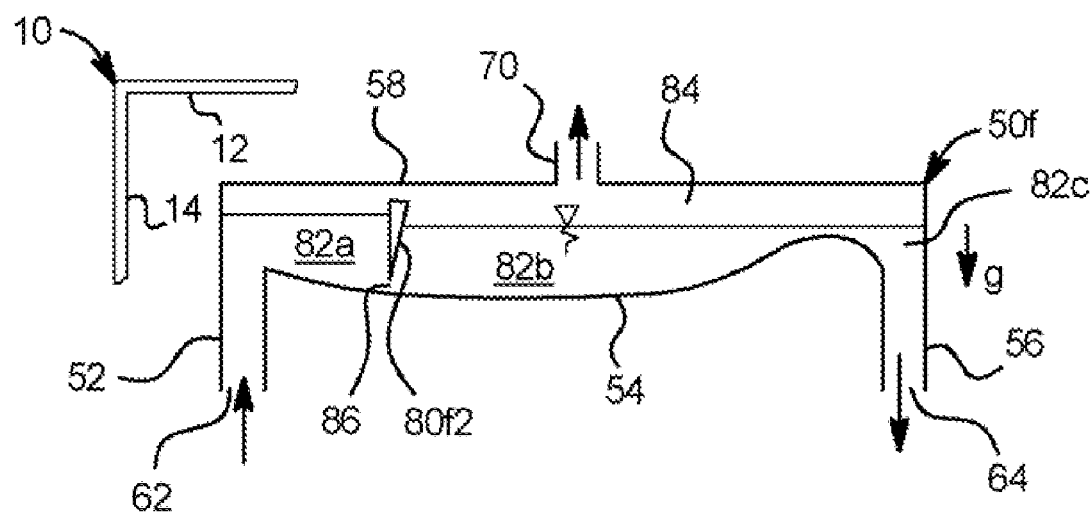
FIG. 6 is yet another elevation view of one embodiment of a dialysis fluid air trap of the present disclosure.

Air separation chamber 50f of FIG. 6 operable with cassette 10 is very similar to air separation chamber 50e of FIG. 5. Here however, second baffle plate 80e3 is not provided and instead curved wall 54 includes a hump at its exit side to decrease dead zones in the fluid flow in region 82b (i.e., areas of low or no fluid flow or stagnation). Also, baffle 80f2 is modified to have a triangular shape, further decreasing the dead zones and increasing circulation zones. Angled exit 82c increases the amount of air bubbles that ride upwardly along the outlet-side surface of baffle 80f2 because the drag force along the baffle 80f2 and the buoyancy force are not co-linear. Outlet flowpath 64 angled as shown tends to lengthen the exit flow path, between baffle 80f2 and outlet wall 56, of chamber 50e since in this configuration buoyancy and drag forces acting on the air bubbles are not in opposite directions. The buoyancy force is always opposite to the direction of gravity whereas the drag force is opposite the velocity of a particle. The bubbles would rise up and they will only feel a smaller component of the drag force opposing their rise.

Air separation chamber 50g of FIG. 7 operable with cassette 10 illustrates a further modification of the air separation chamber 50e of FIG. 5. Here, three polygonal baffles 80g1 to 80g3 are each polygonal shape and positioned to create free flow regions. Again, the angled surfaces of polygonal baffles 80g1, 80g2 and 80g3 increase the ability of those surfaces to carry bubbles upward due to a drag force and buoyancy force differential. In this configuration, buoyancy and drag forces acting on the air bubbles are not in opposite directions. The buoyancy force is always opposite to the direction of gravity whereas the drag force is opposite the velocity of a particle. The bubbles would rise up and they will only feel a smaller component of the drag force opposing their rise. FIG. 7 further illustrates that once diameter D1 and length L are determined, the dimensions of each of the baffles 80g1, 80g2 and 80g3 as well as inlet wall 52, outlet wall 56, bottom wall 54 and top wall 58 are also set. Fluid in regions 82a and 82b can fill to the dimensions shown, with the fluid in region 82a filling to a slightly higher level.

The flow pattern of air separation chamber 50g is similar to that of chambers 50e and 50f. In a similar manner, dialysis fluid 82 is forced from region 82a to region 82b through opening 86, allowing the dialysis fluid 82 to fill and de-gas for a second time in region 82b. Dialysis fluid 82 eventually rises to the free end of polygonal baffle 80g3 and flows over baffle 80g3 to outlet pathway 64. Depending on the dialysis fluid flowrate into region 82c, the fluid level in the region may be the same as (as shown) or lower than that of 82b. Region 82c aids in de-gassing any air bubbles remaining in the dialysis fluid 82.

Air separation chamber 50h of FIG. 8 operable with cassette 10 shows a further modification over these air separation chambers of FIGS. 5 to 7. Here, outlet wall 56 is also angled to help air bubbles travel upwards towards air collection portion 84 via third flow region 82c. Similar to air separation chamber 50g, air separation chamber 50h includes three polygonal baffles 80h1 to 80h3, which are each positioned to create free flow regions.

Figure 9:
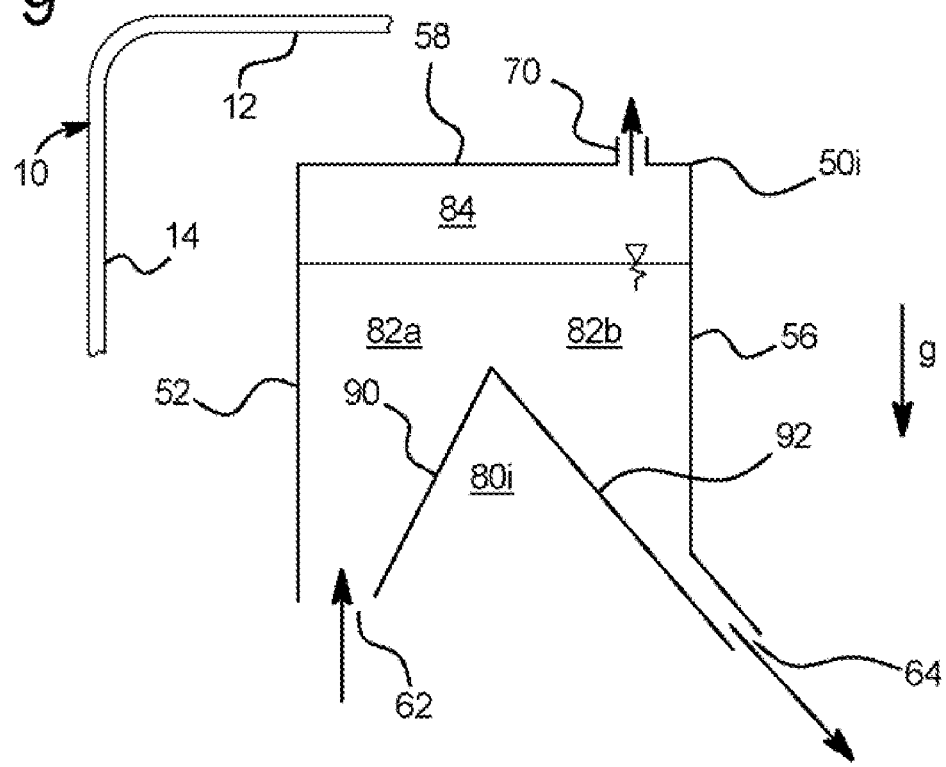
FIG. 9 is a ninth elevation view of one embodiment of a dialysis fluid air trap of the present disclosure.

Referring now to FIG. 9, air separation chamber 50i operable with cassette 10 illustrates one preferred air separation chamber of the present disclosure. While chambers 50e to 50h of FIGS. 5 to 8 are very effective at removing air from dialysis fluid 82, chambers 50e to 50h consume a fair amount of space within cassette 10. It is desirable from a manufacturability and cost standpoint to make cassette 10 smaller rather than larger. It has been found that the first portion of air separation chambers 50g and 50h alone provides a very effective air removal chamber. Thus it is believed that air separation chamber 50i provides a smaller but effective chamber. Similar structures to air separation chamber 50i are included in first regions 82a of chambers 50g and 50h and are also very effective in removing gas bubbles from the fluid as discussed above.

Air separation chamber 50i as seen includes polygonal baffle 80i, which has a triangular shape, including angled inlet surface 90 and angled outlet surface 92. Surfaces 90 and 92 can be straight (as shown) or curved. Angled inlet surface 90 forms a first dialysis fluid region 82a with inlet wall 52. The angled wall provides an increase in the cross-sectional flow area that slows the dialysis fluid 82 as it rises within region 82a.

Angled outlet surface 92 forms a second dialysis fluid region 82b with outlet wall 56. As fluid fills past the apex of baffle 80i, the cross-sectional area approximately doubles, further slowing the flow of dialysis fluid 82 and allowing buoyancy forces to push air bubble from the fluid. Fluid exit 64 extends the outlet flow path similar to air separation chamber 52d such that the flow path is extended as much as possible in the air trap. Fluid pathway 64 acts as a constricted exit having a smaller cross-sectional area as compared with fluid inlet 62. Air collects in region 84 and is purged through air purge line 70.

As seen additionally in FIGS. 7 and 8, in one implementation if inlet wall 52 and top wall 58 are each 2L in length, sides 90 and 92 have a vertical component of length L. The apex of baffle 80i or the intersection of sides 90 and 92 occurs approximately at a distance L from inlet wall 52 and outlet wall 56. This implementation as seen below strikes an effective balance by separating chamber 50i into different regions while allowing an ample common area for dialysis fluid 82 to release air bubbles at the interface with air collection portion 84.

Figure 10:
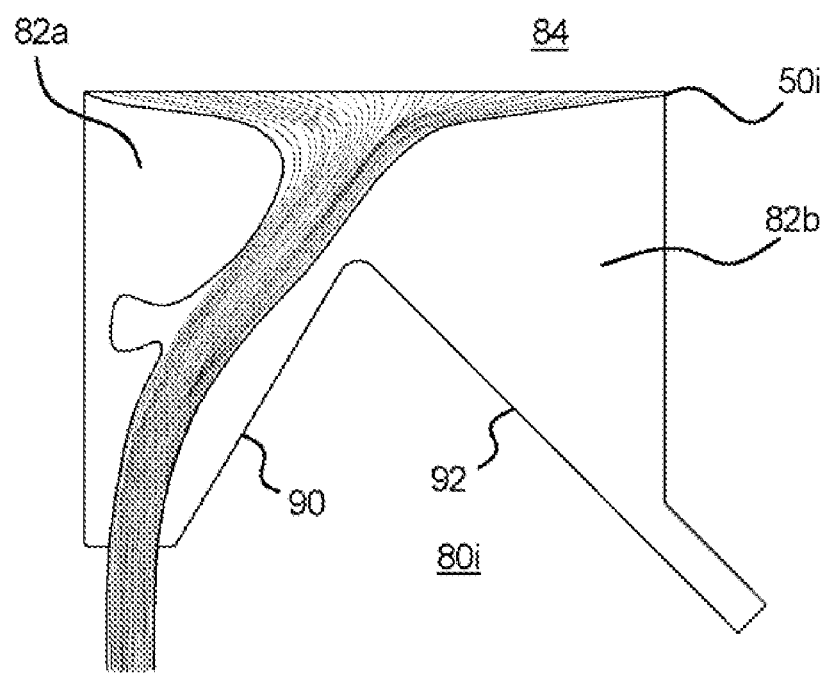
FIG. 10 is simulations of the dialysis fluid air trap of FIG. 9 in operation.

FIG. 10 illustrates an output of a simulation of air separation chamber 50i, showing pathways taken by larger air bubbles, approximately five-hundred microns in diameter, trapped within dialysis fluid 82 when flowing through air separation chamber 50i at a certain flowrate and a certain fluid level.

Referring now to FIG. 11, air separation chamber 50j operable with cassette 10 illustrates an additional concept of providing a nozzle 74 at inlet 62. Nozzle 74 creates a mist or spray of fluid leaving the nozzle due to the low pressure at the exit of the nozzle. The formation of the spray causes de-gassing of the dialysis fluid 82 due to the increased dialysis surface area that the mist creates, and in particular in combination with a negative pressure that may be present in chamber 50j, which would help to pull air from the fluid. One embodiment for providing a nozzled flow into an air separation chamber is described in co-pending application entitled "Dialysis System Having Non-Invasive Fluid Velocity Sensors", Ser. No. 11/876,619, filed Oct. 22, 2007, the pertinent portions of which are incorporated here expressly by reference. Nozzle 74 sprays inlet dialysis fluid 82 against a splash wall 76. Splash wall 76 causes air to de-gas from the dialysis fluid 82 due to impact and also protects against fluid spray exiting through air line 70.

Dialysis fluid 82 falling down along splash plate 76 pools in a first liquid region 82*a*. A baffle 80*j* forces the pooled fluid from region 82*a* through opening 86 caused by baffle 80*j* into a second liquid region 82*b*. Fluid region 82*b* provides another opportunity for liquid to de-gas due to buoyancy forces before the dialysis fluid 82 leaves exit fluid pathway 64.

Nozzle 74 may cause the exiting fluid to foam, which would not be desirable for de-gassing blood in an HD blood circuit for example. However, air separation chamber 50*j* is suitable for any dialysate circuit.

Figure 13:
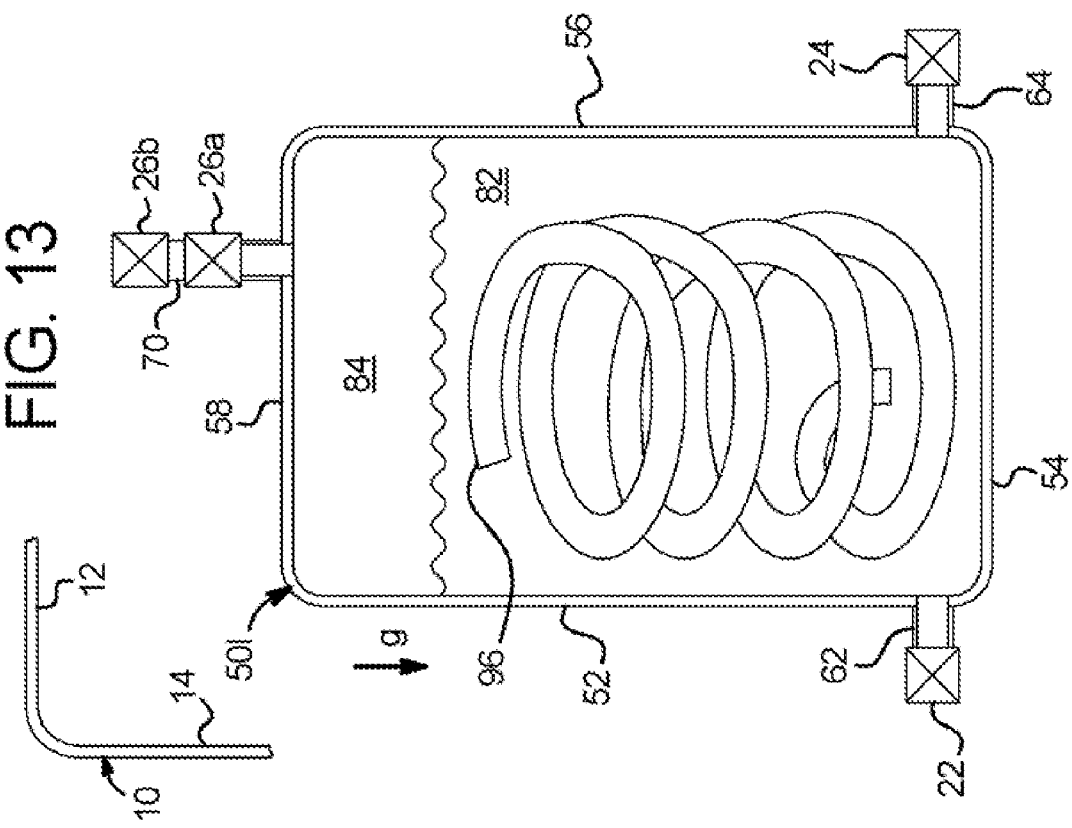
FIG. 13 is a twelfth elevation view of one embodiment of a dialysis fluid air trap of the present disclosure.

Referring now to FIGS. 12 and 13, air separation chambers 50*k* and 50*l*, each operable with dialysis fluid cassette 10 illustrate further alternative embodiments of the present disclosure. Air separation chamber 50*k* of FIG. 12 includes textured spheres or members 94, which are placed loosely within air separation chamber 50*k*. That is, spheres or members 94 are free to move within chamber 50*k*. The particles are sized so as not to be able to fit into, or block flow through, any of inlet line 62, outlet line 64 or air line 70. Suitable spheres can be obtained from McMaster-Carr, model number 9587K13, 1383K44, or similar. Spheres or members 94 introduce additional surface area for bubbles to attach to and be pulled from dialysis fluid 82. Spheres 94 also serve to agitate fluid flow through chamber 50*k*, which has the dual benefit of precipitating air that may be dissolved in the fluid and dislodging and/or coalescing bubbles that may have accumulated on the interior chamber surface or sphere surface. The bubbles move upwardly and eventually de-gas into air portion 84. Spheres or members 94 also agitate the flow of liquid within air separation chamber 50*k*, which also helps to free air bubbles from the dialysis fluid 82.

Air separation chamber 50*l* of FIG. 13 illustrates a helical or coiled ramp 96, which can be textured to produce additional surface area. Ramp 96 in one embodiment is free to move within chamber 50*l*. Ramp 96 can be made of a suitable medical grade plastic, such as any of the material listed above for the rigid portion of cassette 10. Ramp 96 pulls bubbles out of the dialysis fluid 82 and also serves to turbulate or agitate fluid flow through chamber 50*l*.

Figure 14:
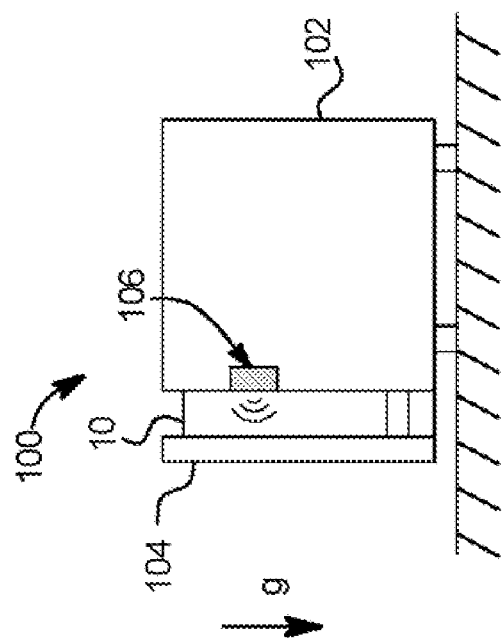
FIG. 14 is an elevation view of a dialysis instrument and cassette operable with the instrument, wherein the instrument includes a vibrator for vibrating the disposable cassette to remove air from fluid flowing through the cassette.

Referring now to FIG. 14, dialysis machine 100 illustrates a further alternative air separation apparatus and technique of the present disclosure. Dialysis machine 100 includes a main or instrument portion 102 and a door 104, which opens and closes with respect to main portion 102 to accept cassette 10. Cassette 10 can have any of the air separation chambers 50 discussed above. In an embodiment, the air separation chamber in operation is pressed against a contact transducer or vibrator 106, which is configured to vibrate the liquid 82 at the air separation chamber. One suitable contract transducer 106 is provided by Xactec Corporation, model number CM-HP-1/2-1.00. While one preferred embodiment is to vibrate the liquid at the air separation chamber 50, it should be appreciated that contract transducer 106 can be configured to shake the entire cassette 10 or other portions of the cassette, such as a pump chamber to relieve air bubbles from the dialysis fluid 82.

It is accordingly contemplated to provide a multi-prong attack for removing and trapping air from dialysis liquid. Each of: (i) inducing vibrations into the air separation chamber; (ii) providing the baffles for buoyancy removal; and/or (iii) providing the nozzle (with any of the air separation chambers 50 described herein) to mist the dialysis fluid 82 into a spray and to increase fluid surface area, ultimately enables the gas to more readily pull from the fluid via negative pressure in order to remove gas from the liquid.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid delivery system comprising:
a fluid disposable configured to hold and transport a medical fluid; and
an air separation chamber in fluid communication with the fluid disposable, the air separation chamber including at least one fluid baffle floating within the air separation chamber and configured to separate air from medical fluid traveling through the chamber, wherein the at least one floating fluid baffle includes: (i) plural particles, (ii) a coiled strip, or (iii) a twisted strip.

2. The medical fluid system of claim 1, wherein the at least one fluid baffle is textured to produce additional surface contact area for removing air from the medical fluid.

3. The medical fluid system of claim 1, which is a hemodialysis system, the fluid disposable configured to transport blood.

4. The medical fluid system of claim 1, which includes an instrument configured to pump the medical fluid through the fluid disposable.

5. The medical fluid system claim 1, wherein the plural particles are at least substantially spherically shaped.

6. The medical fluid system of claim 1, wherein the air separation chamber includes a chamber bottom, a chamber top, a fluid inlet, a fluid outlet and an air vent, at least one of the fluid inlet and the fluid outlet located nearer the chamber bottom than the chamber top, and the vent located nearer the chamber top than the chamber bottom.

7. The medical fluid system of claim 1, wherein the fluid disposable includes a rigid portion, the at least one floating fluid baffle moveable independent from the rigid portion of the fluid disposable.

8. The medical fluid system of claim 1, wherein the air separation chamber is part of the fluid disposable.

9. The medical fluid system of claim 1, wherein the fluid disposable includes a flexible pumping sheet.

10. A medical fluid delivery system comprising:
an instrument configured to pump medical fluid through an air separation chamber, the air separation chamber including at least one fluid baffle floating within the air separation chamber and configured to separate air from the medical fluid pumped through the chamber, wherein the floating fluid baffle includes: (i) plural particles, (ii) a coiled strip, or (iii) a twisted strip.

11. The medical fluid system of claim 10, including a fluid disposable configured to hold and transport the medical fluid, the instrument configured to pump the medical fluid through the fluid disposable.

12. The medical fluid delivery system of claim 11, wherein the air separation chamber is part of the fluid disposable.

13. The medical fluid delivery system of claim 11, which is a hemodialysis system, the fluid disposable configured to transport blood.

14. The medical fluid delivery system of claim 10, wherein the floating fluid baffle is textured to produce additional surface contact area for removing air from the medical fluid.

15. The medical fluid delivery system of claim 10, wherein the plural particles are at least substantially spherically shaped.

16. The medical fluid delivery system of claim 10, wherein the air separation chamber includes a fluid inlet, a fluid outlet and an air vent, the plural particles sized to have a diameter larger than a diameter of the inlet, the outlet or the air vent.

17. A fluid delivery method comprising:
flowing a medical fluid;
removing air from the medical fluid using buoyancy forces; and
floating at least one coiled or twisted strip in the fluid to remove air from the medical fluid by disrupting the flow of medical fluid.

18. The fluid delivery method of claim 17, wherein the medical fluid is a dialysis fluid and which includes pumping the dialysis fluid past the at least one floating baffle.

19. The fluid delivery method of claim 18, wherein the medical fluid is blood and which includes pumping the blood past the at least one coiled or twisted strip.

20. The fluid delivery method of claim 18, which includes floating a plurality of at least substantially spherically shaped particles in the medical fluid.

21. A medical fluid delivery system comprising:
a fluid disposable configured to hold and transport a medical fluid; and
an air separation chamber in fluid communication with the fluid disposable, the air separation chamber including at least one fluid baffle floating within the air separation chamber and configured to separate air from medical fluid traveling through the chamber, wherein the at least one fluid baffle is textured to produce additional surface contact area for removing air from the medical fluid.

22. A medical fluid delivery system comprising:
a fluid disposable including a flexible pumping sheet, the fluid disposable configured to hold and transport a medical fluid; and
an air separation chamber in fluid communication with the fluid disposable, the air separation chamber including at least one fluid baffle floating within the air separation chamber and configured to separate air from medical fluid traveling through the chamber.

23. A fluid delivery method comprising:
flowing a medical fluid;
removing air from the medical fluid using buoyancy forces; and
floating a plurality of at least substantially spherically shaped particles in the fluid to remove air from the medical fluid by disrupting the flow of medical fluid.

* * * * *